US012104022B2

(12) United States Patent
Wan et al.

(10) Patent No.: US 12,104,022 B2
(45) Date of Patent: Oct. 1, 2024

(54) CHIRAL RESOLUTION METHOD MIMICKING MAGNETIC BENEFICIATION AND THE MAGNETIC NANO-INHIBITORS FOR SELECTIVE ENRICHMENT

(71) Applicant: PEKING UNIVERSITY, Beijing (CN)

(72) Inventors: Xinhua Wan, Beijing (CN); Xichong Ye, Beijing (CN); Bowen Li, Beijing (CN); Jie Zhang, Beijing (CN)

(73) Assignee: PEKING UNIVERSITY, Beijing (CN)

( * ) Notice: Subject to any disclaimer, the term of this patent is extended or adjusted under 35 U.S.C. 154(b) by 907 days.

(21) Appl. No.: 17/267,156

(22) PCT Filed: Apr. 9, 2019

(86) PCT No.: PCT/CN2019/081847
§ 371 (c)(1),
(2) Date: Feb. 9, 2021

(87) PCT Pub. No.: WO2020/048126
PCT Pub. Date: Mar. 12, 2020

(65) Prior Publication Data
US 2021/0163695 A1 Jun. 3, 2021

(30) Foreign Application Priority Data
Sep. 3, 2018 (CN) .......................... 201811018745.5

(51) Int. Cl.
C08J 3/215 (2006.01)
B03C 1/005 (2006.01)
B03C 1/01 (2006.01)
B03C 1/015 (2006.01)
B03C 1/02 (2006.01)
B03C 1/035 (2006.01)
B03C 1/28 (2006.01)
B82Y 30/00 (2011.01)
C07B 57/00 (2006.01)
C07C 227/34 (2006.01)
C07C 231/20 (2006.01)
(Continued)

(52) U.S. Cl.
CPC ............... *C08J 3/215* (2013.01); *B03C 1/005* (2013.01); *B03C 1/01* (2013.01); *B03C 1/015* (2013.01); *B03C 1/02* (2013.01); *B03C 1/035* (2013.01); *B03C 1/286* (2013.01); *C07B 57/00* (2013.01); *C07C 227/34* (2013.01); *C07C 231/20* (2013.01); *C07C 231/24* (2013.01); *C08F 212/08* (2013.01); *C08F 220/56* (2013.01); *C08F 220/58* (2013.01); *C08F 293/005* (2013.01); *C08J 3/245* (2013.01); *C08K 3/22* (2013.01); *C08K 5/09* (2013.01); *C08K 9/10* (2013.01); *B03C 2201/18* (2013.01); *B03C 2201/26* (2013.01); *B82Y 25/00* (2013.01); *B82Y 30/00* (2013.01); *B82Y 40/00* (2013.01); *C07B 2200/07* (2013.01); *C07C 237/06* (2013.01); *C08F 220/603* (2020.02); *C08F 2438/03* (2013.01); *C08J 2325/08* (2013.01); *C08K 2003/2275* (2013.01); *C08K 2201/003* (2013.01); *C08K 2201/01* (2013.01); *C08K 2201/011* (2013.01)

(58) Field of Classification Search
CPC ........ C08J 3/215; C08J 3/245; C08J 2325/08; B03C 1/015; B03C 1/02; B03C 2201/18; B03C 2201/26; B03C 1/01; B03C 1/035; B03C 1/286; B03C 1/005; C07B 57/00; C07B 2200/07; C07C 231/24; C07C 237/06; C07C 227/34; C07C 231/20; C08F 212/08; C08F 220/56; C08F 220/58; C08F 220/603; C08F 2438/03; C08F 293/005; C08K 3/22; C08K 5/09; C08K 9/10; C08K 2003/2275; C08K 2201/003; C08K 2201/01; C08K 2201/011; B82Y 30/00; B82Y 40/00; B82Y 25/00
See application file for complete search history.

(56) References Cited

FOREIGN PATENT DOCUMENTS

| CN | 101574645 A | 11/2009 |
|----|-------------|---------|
| CN | 101942029 A | 1/2011 |

(Continued)

OTHER PUBLICATIONS

International Search Report issued in corresponding International Application No. PCT/CN2019/081847; mailed Jun. 27, 2019; State Intellectual Property Office of the P.R. China, Beijing, China, 5 pgs.
Office Action for corresponding Chinese Application No. 201810712104.3; mailed Jun. 12, 2020; 46 pgs.
Ye, Xichong et al. "Self-Reporting Inhibitors: A Single Crystallization Process to Obtain Two Optically Pure Enantiomers"; Angewandte Chemie International Edition, vol. 57(27), Jul. 2, 2018, 8120-8124.
(Continued)

Primary Examiner — Rabon A Sergent
(74) Attorney, Agent, or Firm — HAUPTMAN HAM, LLP

(57) ABSTRACT

A core-shell nanocomposite is formed by co-assembly of an amphiphilic polymer and hydrophobically modified magnetic nanoparticles, with its core being a hydrophobically modified magnetic nanomaterial and its shell being the amphiphilic polymer, wherein hydrophilic segments in the amphiphilic polymer are located at an outermost layer of the shell. The above composite can be used as additives in the crystallization of conglomerates and obtain optically pure crystals of both enantiomers in a single process. The key thereof is that the composite is used to enrich molecules with the same configuration while inhibit the crystallization of the other enantiomer in a supersaturated solution of conglomerates, such that a non-magnetic crystal and a magnetic crystal (which are enantiomers of each other) are generated in a unit operation. Optically pure crystals of both enantiomers with over 90 ee % can be obtained by one-time crystallization, and the total yield can be as high as 40%.

9 Claims, 4 Drawing Sheets

(51) Int. Cl.

| | |
|---|---|
| C07C 231/24 | (2006.01) |
| C08F 212/08 | (2006.01) |
| C08F 220/56 | (2006.01) |
| C08F 220/58 | (2006.01) |
| C08F 293/00 | (2006.01) |
| C08J 3/24 | (2006.01) |
| C08K 3/22 | (2006.01) |
| C08K 5/09 | (2006.01) |
| C08K 9/10 | (2006.01) |
| B82Y 25/00 | (2011.01) |
| B82Y 40/00 | (2011.01) |
| C07C 237/06 | (2006.01) |
| C08F 220/60 | (2006.01) |

(56) References Cited

FOREIGN PATENT DOCUMENTS

| | | |
|---|---|---|
| CN | 104387535 A | 3/2015 |
| WO | 2008/034675 A1 | 3/2008 |

OTHER PUBLICATIONS

Zhu, Lili; "Preparation and application of the electrochemical sensor based on magnetic molecularly imprinted nanoparticles"; China Doctor Dissertation Full-text Database, Dec. 15, 2014, vol. 12, 19-26, 67-78.

Cui, Ning et al. "Preparation, characterization, and biocompatibility evaluation of poly(N-acryloyl-L-lysine)/hyaluronic acid interpenetrating network hydrogels"; Carbohydrate Polymers, Jan. 31, 2016, vol. 136(20), 1017-1026. Zhang, Dongyue, et al.; "Chiral Microspheres Consisting Purely of Optically Active Helical Substituted Polyacetylene: The First Preparation via Precipitation Polymerization and Application in Enantioselective Crystallization"; Macromolecules 2012, 45, 7329-7338.

Addadi, Lia et al, "Useful Impurities of Optical Resolution"; .J. Am. Chem. Soc. 1981; 103, 1248-1249.

Ye, Xichong, et al; "Self-Reporting Inhibitors: A Single Crystallization Process to Obtain Two Optically Pure Enantiomers", Angewandte Chemie Int. Ed. 2018, 57, 8120-8124.

Beesley, Thomas, et al. "Chiral Separation Techniques", Ganapathy Subramanian, 3rd edition, Wiley, 2007: 1-617.

formula I

CHIRAL RESOLUTION METHOD MIMICKING MAGNETIC BENEFICIATION AND THE MAGNETIC NANO-INHIBITORS FOR SELECTIVE ENRICHMENT

RELATED APPLICATIONS

The present application is a National Phase of International Application Number PCT/CN2019/081847 filed Apr. 9, 2019 and claims priority to Chinese Application Number 201811018745.5 filed Sep. 3, 2018.

FIELD OF THE INVENTION

The present invention belongs to the technical field of chiral resolution, and in particular relates to a chiral resolution method mimicking magnetic beneficiation and the magnetic nano-inhibitor for selective enrichment.

BACKGROUND OF THE INVENTION

Optically pure compounds play a significant role in pharmaceuticals, food additives, catalysts, fragrances, pesticides, and chiral displays, etc. At present, selective crystallization is still the most economical and convenient method to provide large-scale chiral compounds (Ganapathy Subramanian, Chiral Separation Techniques, 3rd edition, Wiley, 2007: 59). Among all the sub-strategies, preferential crystallization (including heteronucleation assisted by nanoparticles) and "tailor-made" additives for selective inhibition are wildly used to separate conglomerates. In the 1980s, Lahav et al. (Lia Addadi, Jan van mil, Meir Lahav, *J. Am. Chem. Soc.*, 103 (5), 1981: 1249) raised the theory of "Rule of Reversal", and developed "tailor-made" additives for delaying the crystallization of the molecules with the same configuration, while allowing crystallization of the molecules with the opposite configuration. Thus, optically pure crystals can be obtained. Mastai et al. developed a kind of nano particles consisted of chiral polymers, crystals with the opposite configuration were obtained in some cases, however, the ee % values were low. Jianping Deng et al. (Dongyue Zhang, Ci Song, Jianping Deng, *Macromolecules*, 45, 2012: 7329) reported the enantioselective crystallization of alanine regulated by polyacetylene chiral nanospheres. The chiral nanospheres played the role of "seeds" and existed in the crystals with the same configuration. The team of the inventor(s) of the present invention once reported a kind of graft copolymers with polymethylsiloxane as main chain and triethylene glycol and Poly[$N^6$-methacryloyl-L-lysine] as side chains, which could form a core-shell assembly in supersaturated solution of amino acids. When the grafted copolymers were used as additives to regulate the crystallization of amino acids, colorless R-crystals and colored S-crystals could be obtained successively. Two optically pure enantiomers can be obtained in one crystallization process (Xichong Ye, Jiaxi Cui, Bowen Li, Na Li, Jie Zhang, Xinhua Wan, *Angew. Chem. Int. Ed.* 2018, 57, 8120-8124; patent application No.: 201710542082.6). However, there are still problems like the difficulty in synthesis, low stability, limited application scopes, time-consuming and laborious.

SUMMARY OF THE INVENTION

One objective of the present invention is to provide a magnetic nano-inhibitor for selective enrichment.

The magnetic nano-inhibitor provided by the present invention is a core-shell nanocomposite formed by the co-assembly of amphiphilic polymers and hydrophobically modified magnetic nanoparticles, with its core being a hydrophobically modified magnetic nanomaterial, and its shell being the amphiphilic polymers, wherein hydrophilic segments of the amphiphilic polymers are located at an outermost layer of the shell.

Crosslinking reactions may also occur between the above hydrophilic segments at the outermost layer to further provide organic-inorganic hybrid nanoparticles having a stable structure.

The structure diagram of the magnetic nano-inhibitor is shown in formula I, see FIG. 8.

The hydrophilic segment can be:

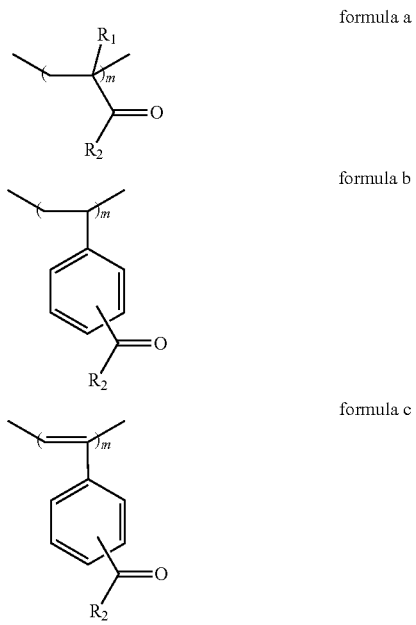

formula a formula b formula c

In formula I, the magnetic nano-inhibitor is named M-A(m)-B(n), wherein M is a chemical formula of the magnetic nanoparticle as used (e.g., Fe, $Fe_3O_4$, $\gamma$-$Fe_2O_3$, etc.); A is an abbreviation of inhibitor segments (hydrophilic segments) (e.g., PMAL, PMPA); m is the polymerization degree of the inhibitor segments; B is the abbreviation of hydrophobic segments (e.g., PS, PMS, etc.); and n is the polymerization degree of the hydrophobic segments.

In the amphiphilic polymer in formula I, the hydrophilic segments are inhibitor segments having the ability of chiral recognition, and can in particular be derivatives of poly(methyl)acrylamide, derivatives of poly(methyl)acrylate, derivatives of polystyrene, derivatives of polyacetylene, etc., with the structural formulas shown in formulas a-c above; and the hydrophobic segments can be polystyrene (PS), polyethylene, polypropylene, polybutadiene, polyisoprene, polydimethylsiloxane, polymethylhydrosiloxane, polymethacrylate, polymethacrylamide, polyamide, polyimide, polyformaldehyde, polycarbonate, cellulose, and their derivatives. Block copolymers, random copolymers, grafted copolymers, hyperbranched polymers, which structures are based on the above polymers' repeating units are also included in the present invention.

In formulas a-c, $R_2$ should be at least one of the groups shown below. (* represents the bonding position). The common feature of these groups is that they can adsorb on specific faces of one enantiomers' nuclei through noncovalent interaction, thus inhibiting their crystallization and further enrichment of these nuclei. Other types of hydrophilic functional groups with the same functions are also included in the present invention. The following structures are provided as examples only:

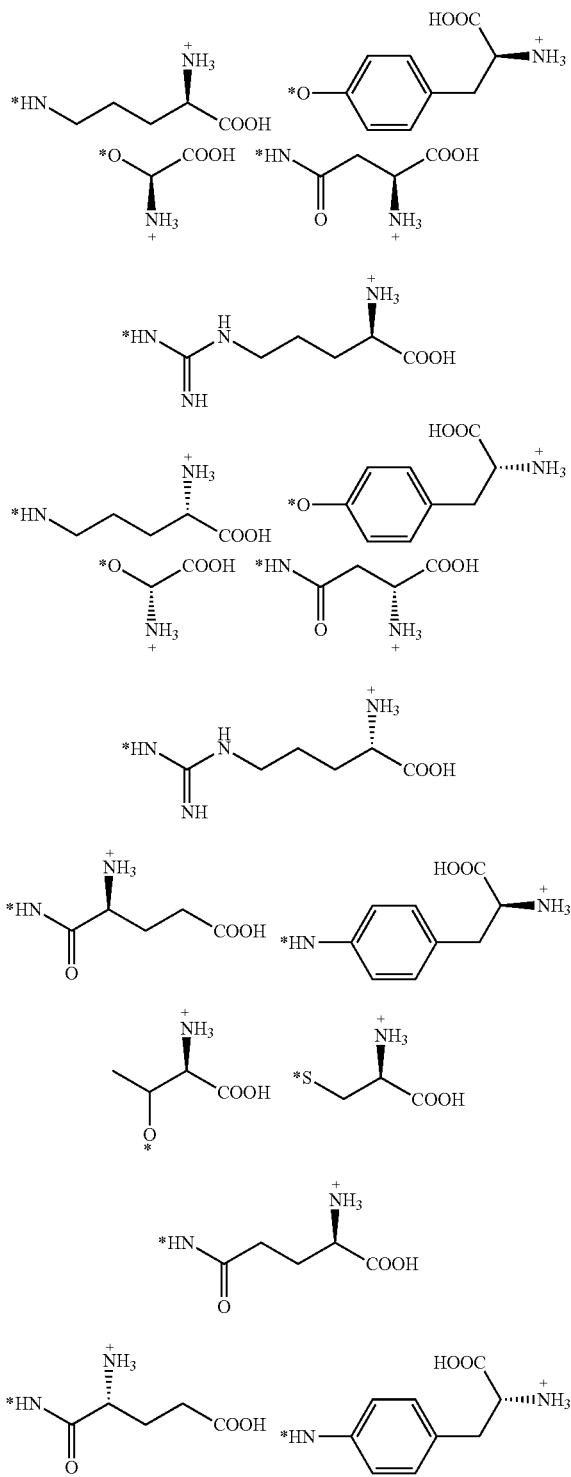

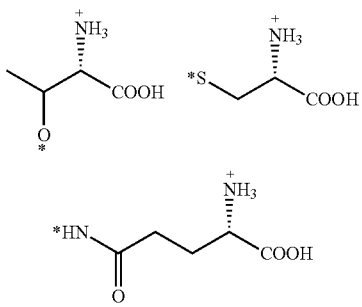

In formula a, $R_1$ can be at least one selected from the group consisting of methyl and hydrogen atoms.

In formula I, m is the polymerization degree of the inhibitor segments, which is in a range from 10 to 60, particularly from 10 to 15, from 15 to 20, from 20 to 25, from 25 to 30, from 30 to 35, from 35 to 40, from 40 to 45, from 45 to 50, from 50 to 55, from 55 to 60.

In formula I, the magnetic cores can be magnetic nanoparticle such as Fe, Co, Ni, FePt, CoPt, FeAu, FePd, $SmCo_5$, $Fe_3O_4$, $\gamma\text{-}Fe_2O_3$, $MFe_2O_4$ (M=Zn, Mn, Ni, Co, etc.), $MO\cdot6Fe_2O_3$ or $MFe_{12}O_{19}$ (M=Ba, Sr, etc.), having a diameter in the range from 3 nm to 500 nm, and in particular from 3 nm to 5 nm, from 5 nm to 10 nm, from 10 nm to 20 nm, from 20 nm to 50 nm, from 50 nm to 100 nm, from 100 nm to 500 nm; the hydrophobic molecule for modification can be at least one selected from the group consisting of oleic acid, oleamine, pyrrolidone, 11,11-dihydroxymethyl undecane, poly(4-vinylpyridine), and block copolymers of poly(4-vinylpyridine) and polyethylene.

Fractional crystallization is the most commonly used method for the resolution of racemic compounds in industry. However, fractional crystallization is in general of low yield, capable of producing only one enantiomer in one operation. However, the "magnetic nano-inhibitor" provided by the present invention can separate the crystallization of a pair of enantiomers in one unit operation. At the beginning of the crystallization process, the hydrophilic segments of the inhibitor can stereoselectively adsorb on specific faces of one enantiomer's nuclei or their aggregates which are under the critical nucleus size to hinder their further crystallization. But the crystallization of the other enantiomer won't be affected. With the crystallization of the other enantiomer, more and more nuclei or aggregates of the former one are enriched by the nano-inhibitors. As a result of Oswald ripening, these nuclei or aggregates will gradually become larger. When the size of these nuclei or aggregates is beyond the critical size, the crystallization of the enantiomer begins and the magnetic nano-inhibitors were embedded in the crystals. When crystallization is finished, a mixture of the two enantiomers is obtained by filtration. One enantiomeric crystal is magnetic and can be attracted by a magnet, and the other remained is non-magnetic.

Another objective of the present invention is to provide a preparation method of the above magnetic nano-inhibitor.

The preparation method provided by the present invention comprises the steps of:

1) dissolving the amphiphilic polymer in a cosolvent to obtain an amphiphilic polymer solution; dispersing the hydrophobically modified magnetic nanoparticles in a cosolvent to obtain a dispersion of the hydrophobically modified magnetic nanoparticles; and 2) mixing the amphiphilic polymer solution with the dispersion of the hydrophobically modified magnetic nanoparticles in proportion to form a mixed solution, and then adding deionized water to the mixed solution until a stable assembly is formed.

In step 1) of the above method, the cosolvent refers to a solvent that can both disperse the hydrophobically modified magnetic nanoparticles and dissolve the amphiphilic polymer. The cosolvent can be at least one selected from the group consisting of DMSO (Dimethyl sulfoxide), DMF (N,N-dimethylformamide), THF (tetrahydrofuran), dioxane, $CH_3CN$, acetone, methanol, ethanol, and isopropanol.

In step 1) of the above method, the "hydrophobically modified magnetic nanoparticles" can be prepared according to an existing method. For example, oleic acid coated $Fe_3O_4$ nanoparticles ($Fe_3O_4$@oleic acid) can be prepared with reference to the document (Shouheng sun, Hao Zeng, David B. Robinson, Simone Raoux, Philip M. Rice, *J. Am. Chem. Soc.* 2004, 126, 273-279).

In step 2) of the above method, the mass ratio of the amphiphilic polymer to the hydrophobically modified magnetic nanoparticles in the mixed solution is in the ranger from 1:0.1 to 1, and in particular can be in the range from 1:1 to 2, from 1:2 to 3, from 1:3 to 4, or from 1:4 to 5.

In step 2) of the above method, the deionized water is preferably dropwise added into the mixed solution. The volume ratio of the mixed solution to the deionized water is in the range from 1:2 to 8, and in particular can be 1:2, 1:4, 1:6, or 1:8.

The method further comprises: adding a crosslinking agent into a reaction system in which the stable assembly is formed to perform a shell crosslinking reaction, followed by dialysis in pure water to remove an organic solvent and unreacted small molecules, centrifugal separation, and freeze drying to obtain a final product (i.e., organic-inorganic hybrid nanoparticles having a stable structure).

The crosslinking agent may be at least one selected from the group consisting of 1-(3-dimethylaminopropyl)-3-ethylcarbodiimide hydrochloride (EDC), and glycol bis 2-aminoethyl ether.

One further objective of the present invention is to provide a new method for chiral separation mimicking magnetic beneficiation with participation of the above magnetic nano-inhibitor.

The new chiral separation method mimicking magnetic beneficiation provided by the present invention comprises the steps of:

(1) dissolving racemic substrate into water until supersaturated, followed by hot filtration;

(2) adding a certain amount of a magnetic nano-inhibitor into the supersaturated solution, followed successively by ultrasonic dispersion, slowly cooling to a crystallization temperature, adding optically pure seeds of the above racemic substrate (if the magnetic enrichment nano inhibitor has S-chiral segments, then R-seeds are added, otherwise S-seeds are added), and standing still for crystallization;

(3) obtaining, after crystallization, a mixture of a colored crystal and a colorless crystal; and (4) approaching the crystal mixtures with a magnet, the colored crystal (one enantiomer) will be attracted by the magnet, and the colorless crystal (the other enantiomer) will not be attracted by the magnet, i.e., the resolution of the two enantiomers is realized.

The method further comprises: dissolving the colored crystal in water, and recycling, by magnetic attraction, the magnetic nano-inhibitor, which can be reused after being washed.

In step (1) of the above method, the concentration of the racemic substrate varies with the width of its metastable zone. Taking asparagine monohydrate as an example, its concentration can be in the range from 50 $mg·mL^{-1}$ to 150 $mg·mL^{-1}$, and in particular can be 59 $mg·mL^{-1}$, 91 $mg·mL^{-1}$, 111 $mg·mL^{-1}$, or 154 $mg·mL^{-1}$, wherein 111 $mg·mL^{-1}$ is the best.

The substrate to be resolved varies with different nano-inhibitors. That is, the molecular structure of the substrate to be resolved and the molecular structure of the inhibitor segments must have certain similarity (i.e., the structure of the side chain of the inhibitor and that of the chiral group of the substrate to be resolved remain similar). Where the inhibitor segment of the polymer is poly($N^6$-methacryloyl-S-lysine hydrochloride) (PMAL·HCl), for example, the substrate to be resolved can be asparagine monohydrate, threonine, etc. Where the inhibitor segment of the polymer is poly(p-methacryloyl-S-phenylalanine hydrochloride) (PMPA·HCl), for example, the substrate to be resolved can be p-hydroxyphenylglycine-p-methylbenzene sulfonate (pHpgpTs), etc.

In step (2) of the above method, the magnetic nano-inhibitor accounts for 0.1-2.0 wt %, in particular 0.1-0.25%, 0.25-0.5%, 0.5-1.0%, 0.1%, 0.5%, 1.0%, 1.5%, or 2.0%, of the racemic substrate to be resolved. The addition amount of the optically pure seeds of the racemic substrate is 0.1-0.5 wt % of the racemic substrate to be resolved.

In step (2) of the above method, the ultrasonic dispersion is performed in water at a temperature in the range from 40° C. to 60° C., at a power in the range from 40 KHz to 80 KHz, and for a period in the range from 15 min to 60 min.

The crystallization is performed at a temperature in the range from 0° C. to 40° C. for a period in the range from 6 h to 144 h.

In step (3) of the above method, after the crystallization, crystals precipitate at the bottom, and an upper liquid is poured out. The crystals at the bottom are transferred to a container with a large bottom surface area (such as a Petri dish), evenly distributed at the bottom of the container as far as possible in a wet state to avoid mutual adhesion, and dried under vacuum.

In step (4) of the above method, the optical purity of the resolved enantiomeric crystals can be determined by optical rotation tests and chiral HPLC.

The present invention uses "the magnetic nano-inhibitor" to inhibit the growth of one enantiomorph, and at the same time, the nuclei of the enantiomer under the critical size can be enriched by the nano-inhibitors. The enantiomer with opposite configuration will crystallized out preferentially. The enriched small nuclei will grow into crystal seeds which are beyond the critical size through Oswald ripening process, and then crystallize out surrounding the nanoparticles to wrap the magnetic nano-inhibitors therein. When the crystals no longer grow, the nanoparticles will then be enriched on a surface of the crystal of a corresponding configuration. This provides both the internal and the surface of the enantiomer crystal with magnetic nanoparticles, rendering it easy to be attracted by a magnet. And the crystal of the other enantiomer is not affected and has no magnetism. In this way, the crystals of two enantiomers, one magnetic and the other non-magnetic, can be obtained in one single crystallization process. The enantiomers can be separated by a method similar to magnetic beneficiation.

It should be understood that within the scope of the present invention, the various technical features aforementioned and various technical features to be described in detail in the following (e.g., in the Examples) of the present

DETAILED DESCRIPTION OF EMBODIMENTS

The present invention will be described in the following through specific examples. However, the present invention is not limited thereto. Any amendment, equivalent replacement, improvement, and the like made within the spirit and principles of the present invention shall be included in the protection scope of the present invention.

The experimental methods used in the following examples are conventional methods unless otherwise specified.

The materials, reagents, and the like used in the following examples can all be obtained commercially without special instructions.

Example 1 Preparation of a Magnetic Enrichment Nano Inhibitor

Figure 1:
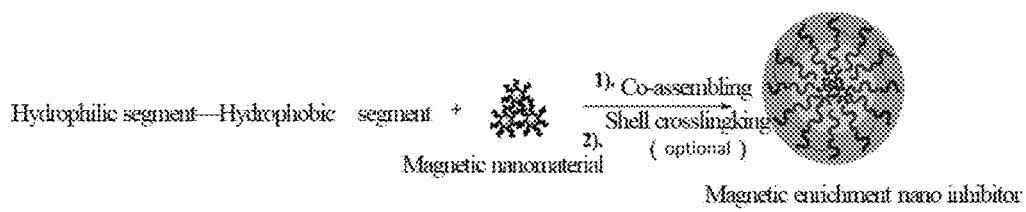
FIG. 1 is a reaction flow chart for preparing a magnetic nano-inhibitor of the present invention.
Figure 1:
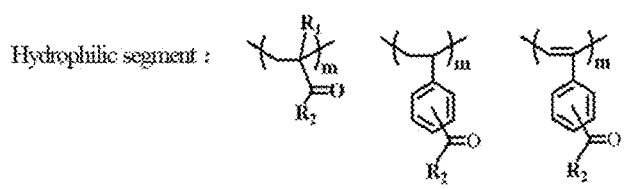
Figure 2:
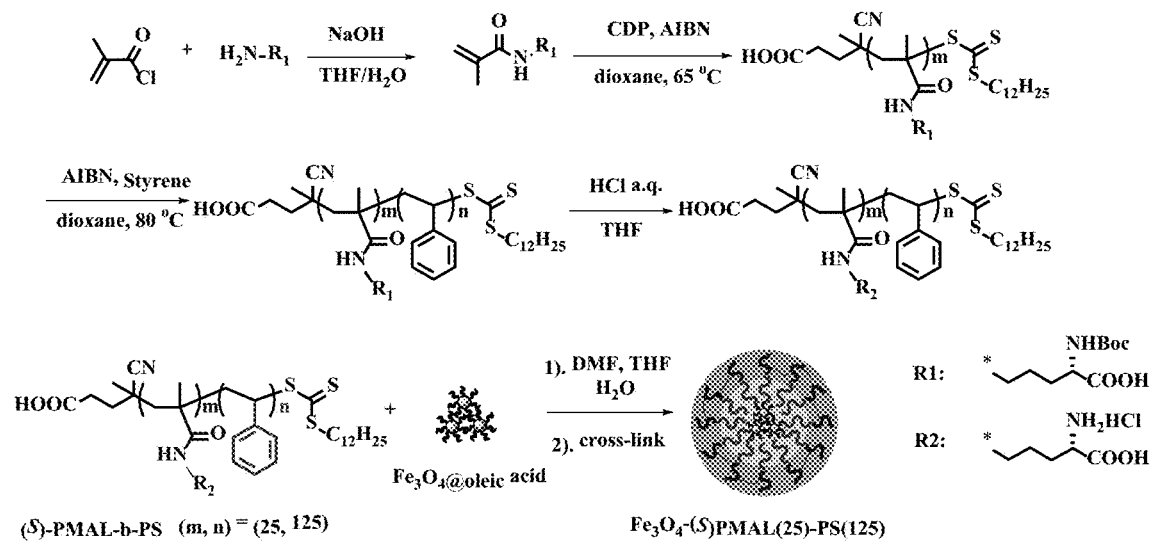
FIG. 2 is a reaction flow chart for preparing a magnetic nano-inhibitor in Example 1.

The preparation was performed according to the flow chart shown in FIG. 2.

(1) (S)-PMAL-b-Ps was obtained by reversible addition and fragmentation chain transfer (RAFT) polymerization. The polymerization degree of inhibitor segments was controlled at 25, and the polymerization degree of PS chain segments was controlled at 125.

(2) Oleic acid coated $Fe_3O_4$ nanoparticles ($Fe_3O_4$@oleic acid) were prepared with reference to the document (Shouheng Sun, Hao Zeng, David B. Robinson, Simone Raoux, Philip M. Rice, *J. Am. Chem. Soc.* 2004, 126, 273-279). The diameter of the nanoparticles was controlled at about 6 nm.

(3) Solution A (50 mg of polymer (S)-PMAL-b-Ps dissolved in 5 mL of DMSO) and solution B (100 mg of $Fe_3O_4$@oleic acid dissolved in 100 mL of THF) were prepared. 5 mL of solution A was taken and added into 45 mL of DMSO for dilution, followed by dropwise addition of 50 mL of solution B and homogeneous mixing. 320 mL of deionized water was dropwise added under stirring within two hours.

(4) An aqueous solution (10 mg/mL) of 1-(3-dimethylaminopropyl)-3-ethylcarbodiimide hydrochloride (EDC) and an aqueous solution (10 mg/mL) of glycol bis 2-aminoethyl ether were prepared. 1.15 mL of the EDC solution and 0.56 mL of the diamine solution were added into the above solution, followed by stirring at room temperature overnight.

(5) The above solution was placed into pure water for dialysis over 48 hours, with the water being changed every three hours. After centrifugation at 15000 rpm, the supernatant was poured, and final product was obtained by freeze drying under vacuum.

Figure 4:
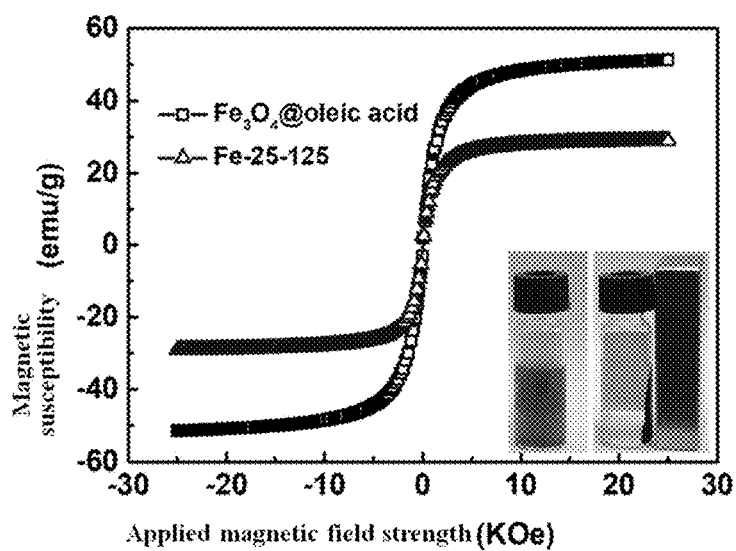
FIG. 4 shows magnetic hysteresis loops of oleic acid coated $Fe_3O_4$ nanoparticles and the magnetic nano-inhibitor prepared in Example 1, as well as pictures thereof dispersed in water and attracted by a magnet.

FIG. 4 shows hysteresis loops of oleic acid coated $Fe_3O_4$ nanoparticles and the magnetic nano-inhibitor prepared in Example 1, and pictures of dispersed nano-inhibitors in water and attracted by a magnet. As can be seen from FIG. 4, both the $Fe_3O_4$ nanoparticles and the magnetic nano-inhibitor as prepared had superparamagnetic properties, i.e., they had high magnetism under an external magnetic field, and the magnetism disappeared immediately once the magnetic field was removed.

Figure 5:
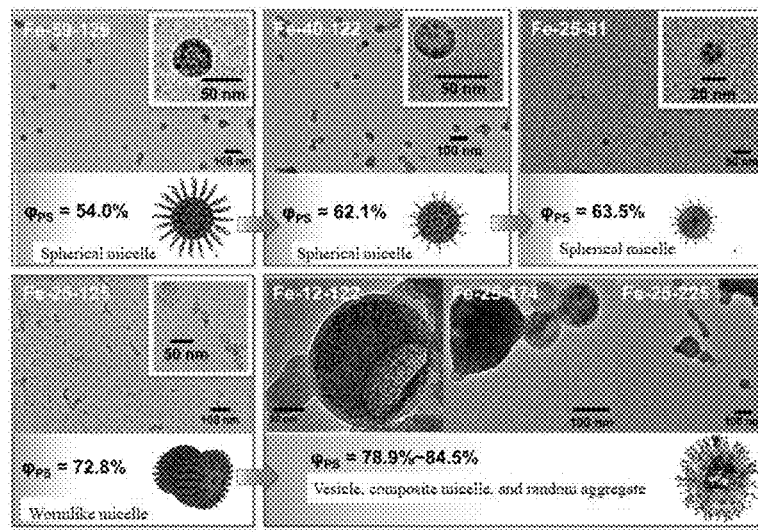
FIG. 5 shows morphologies of polymeric assemblies by using different polymers with various block compositions.

FIG. 5 shows the morphologies of the magnetic nano-inhibitor. As can be seen from the figure, different morphologies could be obtained when polymers with different block ratios were used. Taking (S)-PMAL(25)-b-Ps (125) as an example, wormlike micelles were obtained.

Example 2 Preparation of a Magnetic Enrichment Nano Inhibitor

Figure 3:
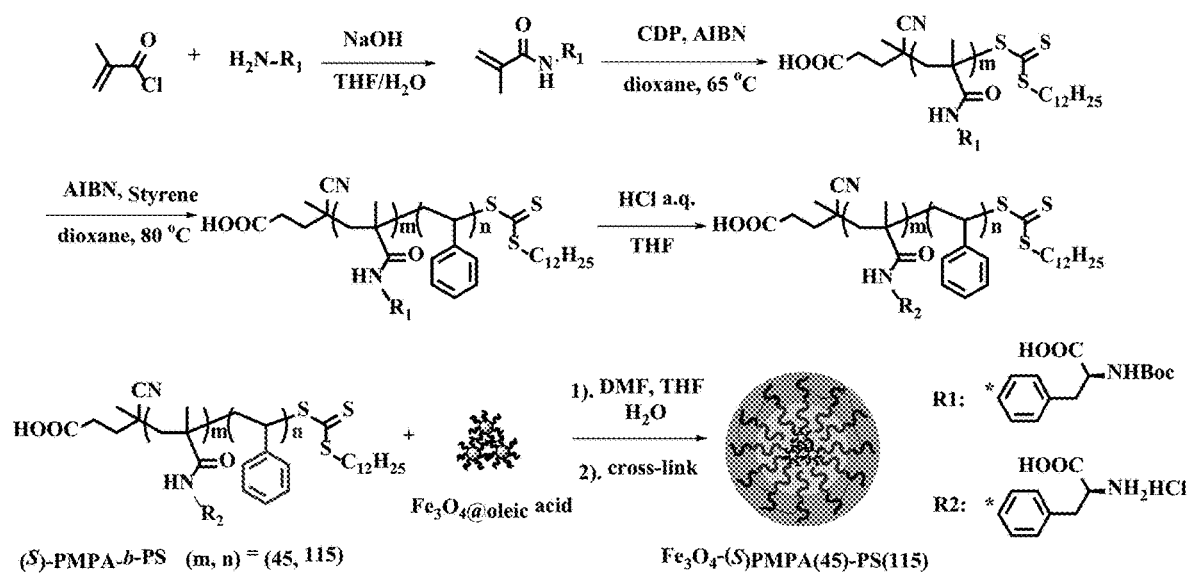
FIG. 3 is a reaction flow chart for preparing a magnetic nano-inhibitor in Example 2.

The preparation was performed according to the flow chart shown in FIG. 3.

(1) (S)-PMPA-b-Ps was obtained by reversible addition and fragmentation chain transfer (RAFT) polymerization. The polymerization degree of inhibitor segments was controlled at 45, and that of PS segments was controlled at 115.

(2) Oleic acid coated $Fe_3O_4$ nanoparticles ($Fe_3O_4$@oleic acid) were prepared with reference to the aforementioned document, the diameter thereof being controlled at about 6 nm.

(3) Solution A (50 mg of polymer (S)-PMPA-b-Ps dissolved in 5 mL of DMSO), and solution B (100 mg of $Fe_3O_4$@oleic acid dissolved in 100 mL of THF) were prepared. 5 mL of solution A was taken and added into 45 mL of DMSO for dilution, followed by dropwise addition of 50 mL of solution B, and homogeneous mixing. 320 mL of deionized water was dropwise added under stirring in two hours.

(4) An aqueous solution (10 mg/mL) of 1-(3-dimethylaminopropyl)-3-ethylcarbodiimide hydrochloride (EDC) and an aqueous solution (10 mg/mL) of glycol bis 2-aminoethyl ether were prepared. 1.15 mL of the EDC solution and 0.56 mL of the diamine solution were added into the above solution, followed by stirring at room temperature overnight.

(5) The above solution was placed into pure water for dialysis over 48 h, with water being changed every three hours. After centrifugation at 15000 rpm, the supernatant was poured, and final product was obtained by freeze drying under vacuum.

Example 3 Resolution of Racemic Asparagine Monohydrate

In this example, $Fe_3O_4$-(S)PMAL(25)-PS(81) was selected as a crystallization additive, and its preparation method was the same as that of Fe$_3$O$_4$-(S)PMAL(25)-PS(125) in Example 1, except that the polymerization degree of PS polymerization chains was 81.

Specific operation steps were as follows.

(1) 9 mL water was added into 1 g racemic asparagine monohydrate, followed by heating to 60° C. and dissolving under sufficient stirring. A clear and transparent supersaturated solution at a concentration of 111 mg/mL was obtained after hot filtering.

(2) 5 g solution obtained in step (1) was taken and added with 10.4 g of nano-inhibitor Fe$_3$O$_4$-(S)PMAL(25)-PS(81) (the content of the inhibitor segments was 0.25 wt % to the racemic substrate), followed by ultrasonic dispersion in 60° C. hot water for 15 min. After slowly cooling to room temperature, 0.5 mg seeds of R-asparagine monohydrate were added in.

(3) The solution obtained in step (2) was stood at 25° C. for 72 h.

(4) After crystallization, crystals precipitated at the bottom and an upper liquid was poured out. The remained crystals were dried under vacuum.

Figure 6A:
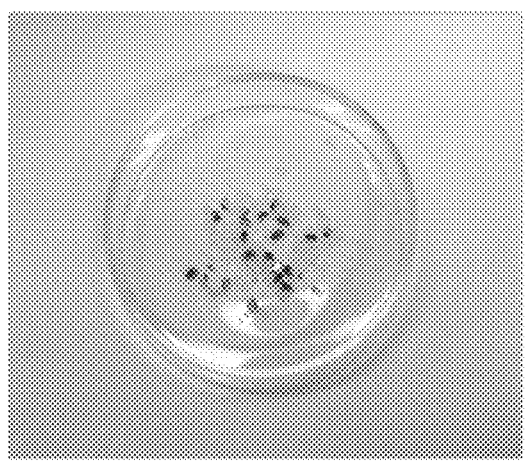
FIG. 6a shows crystal mixture of R-asparagine monohydrate and S-asparagine monohydrate obtained in Example 3, and 6b is a picture of the mixed crystals after being attracted by a magnet, wherein the S-crystals can be attracted and the R-crystals cannot be attracted.
Figure 6B:
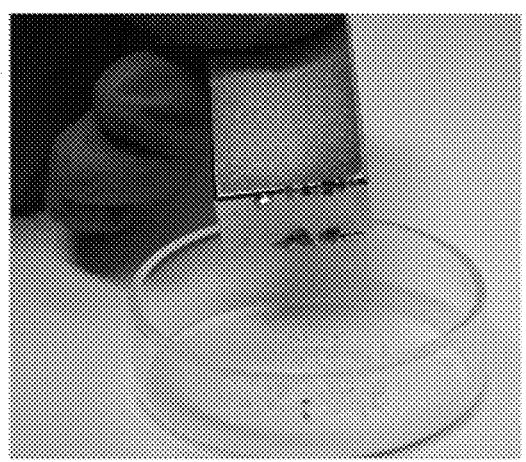

(5) The vessel containing the crystals was taken out, and a magnet (with a surface magnetic field strength >0.3 T) was used to approach the crystal mixture. The colored crystals were attracted by the magnet, while the colorless ones cannot be attracted by the magnet, i.e., resolution of the two enantiomers was effectuated. See FIGS. 6a and 6b.

Figure 7:
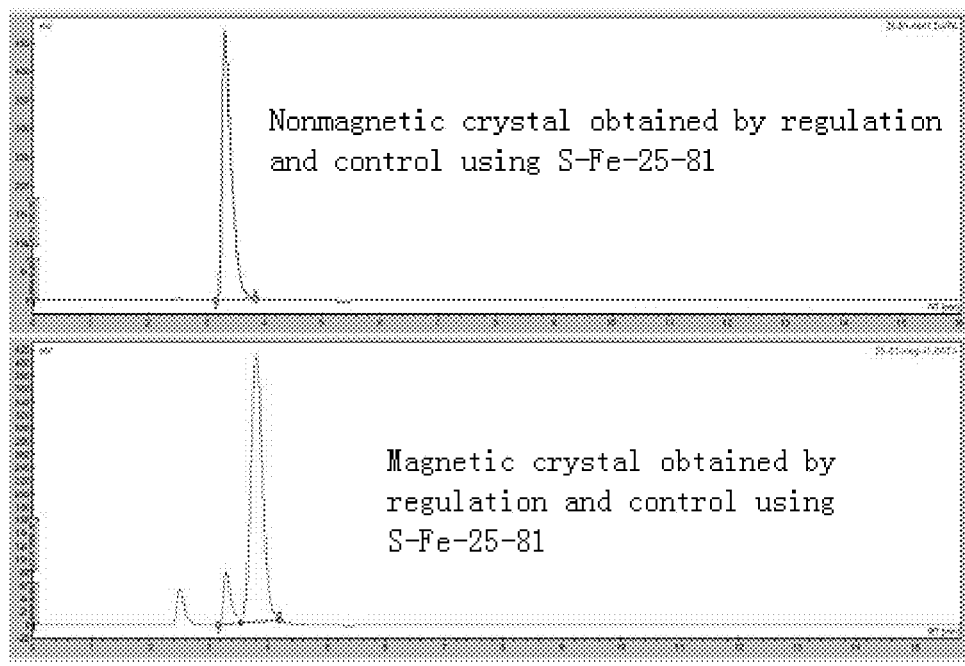
FIG. 7 shows a typical result of crystal ee % value tested by chiral HPLC in Example 3.
Figure 8:
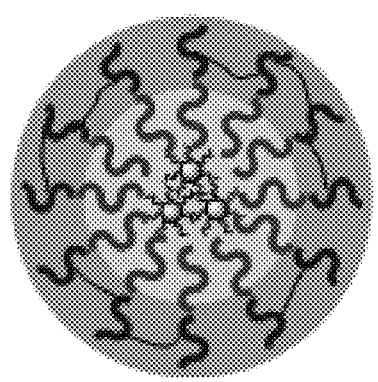
FIG. 8 shows the structure diagram of the magnetic nano-inhibitor, wherein  represents the hydrophobically modified magnetic nanomaterial;  represents a hydrophobic segment; and  represents a hydrophilic segment.

The crystal yields and enantiomeric excess values (Table 1) were calculated in this example, and the enantiomeric excess values were characterized by chiral HPLC (see FIG. 7).

Example 4 Resolution of Racemic Asparagine Monohydrate

In this example, Fe$_3$O$_4$-(S)PMAL(25)-PS(125) in Example 1 was selected as a crystallization additive, and specific operation steps were as follows.

(1) 9 mL water was added into 1 g racemic asparagine monohydrate, followed by heating to 60° C. and dissolving under sufficient stirring. A clear and transparent supersaturated solution at a concentration of 111 mg/mL was obtained after hot filtering.

(2) 5 g solution obtained in step (1) was taken and added with 11.4 g of nano-inhibitor Fe$_3$O$_4$-(S)PMAL(25)-PS(125) ((the content of the inhibitor segments was 0.25 wt %), followed by ultrasonic dispersion in 60° C. hot water for 15 min. After slowly cooling to room temperature, 0.5 mg seeds of R-asparagine monohydrate were added in.

(3) The solution obtained in step (2) was stood at 25° C. for 72 h.

(4) After crystallization, crystals precipitated at the bottom and an upper liquid was poured out. The remained crystals were dried under vacuum.

(5) The vessel containing the crystals was taken out, and a magnet (with a surface magnetic field strength >0.3 T) was used to approach the mixed crystals. The colored crystals were attracted by the magnet, while the colorless crystals cannot be attracted by the magnet, i.e., resolution of the two enantiomers was effectuated.

The crystal yields and enantiomeric excess values (Table 1) were calculated in this example, and the enantiomeric excess values were characterized by chiral HPLC.

Example 5 Resolution of Racemic Asparagine Monohydrate

In this example, Fe$_3$O$_4$-(S)PMAL(25)-PS(174) was selected as a crystallization additive, and its preparation method was the same as that of Fe$_3$O$_4$-(S)PMAL(25)-PS(125) in Example 1, except that the polymerization degree of PS polymerization chains was 174.

Specific operation steps were as follows.

(1) 9 mL water was added into 1 g racemic asparagine monohydrate, followed by heating to 60° C. and dissolving under sufficient stirring. A clear and transparent supersaturated solution at a concentration of 111 mg/mL was obtained after hot filtering.

(2) 5 g solution obtained in step (1) was taken and added with 12.2 g of nano-inhibitor Fe$_3$O$_4$-(S)PMAL(25)-PS(174) (the content of the inhibitor segments was 0.25 wt % to the racemic substrate), followed by ultrasonic dispersion in 60° C. hot water for 15 min. After slowly cooling to room temperature, 0.5 mg seeds of R-asparagine monohydrate were added in.

(3) The solution obtained in step (2) was stood at 25° C. for 72 h.

(4) After crystallization, crystals precipitated at the bottom and an upper liquid was poured out. The remained crystals were dried under vacuum.

(5) The vessel containing the crystals was taken out, and a magnet (with a surface magnetic field strength >0.3 T) was used to approach the crystal mixture. The colored crystals were attracted by the magnet, while the colorless ones cannot be attracted by the magnet, i.e., resolution of the two enantiomers was effectuated. See FIGS. 6a and 6b.

The crystal yields and enantiomeric excess values (Table 1) were calculated in this example, and the enantiomeric excess values were characterized by chiral HPLC.

Example 6 Resolution of Racemic Asparagine Monohydrate

In this example, Fe$_3$O$_4$-(S)PMAL(25)-PS(225) was selected as a crystallization additive, and its preparation method was the same as that of Fe$_3$O$_4$-(S)PMAL(25)-PS(125) in Example 1, except that the polymerization degree of PS polymerization chains was 225.

Specific operation steps were as follows.

(1) 9 mL water was added into 1 g racemic asparagine monohydrate, followed by heating to 60° C. and dissolving under sufficient stirring. A clear and transparent supersaturated solution at a concentration of 111 mg/mL was obtained after hot filtering.

(2) 5 g solution obtained in step (1) was taken and added with 8.7 g of nano-inhibitor Fe$_3$O$_4$-(S)PMAL(25)-PS(225) (the content of the inhibitor segments was 0.25 wt % to the racemic substrate), followed by ultrasonic dispersion in 60° C. hot water for 15 min. After slowly cooling to room temperature, 0.5 mg seeds of R-asparagine monohydrate were added in.

(3) The solution obtained in step (2) was stood at 25° C. for 72 h.

(4) After crystallization, crystals precipitated at the bottom and an upper liquid was poured out. The remained crystals were dried under vacuum.

(5) The vessel containing the crystals was taken out, and a magnet (with a surface magnetic field strength >0.3 T) was used to approach the crystal mixture. The colored crystals were attracted by the magnet, while the colorless ones cannot be attracted by the magnet, i.e., resolution of the two enantiomers was effectuated. See FIGS. 6a and 6b.

The crystal yields and enantiomeric excess values (Table 1) were calculated in this example, and the enantiomeric excess values were characterized by chiral HPLC.

Example 7 Resolution of Racemic Asparagine Monohydrate

In this example, $Fe_3O_4$-(S)PMAL(12)-PS(122) was selected as a crystallization additive, and its preparation method was the same as that of $Fe_3O_4$-(S)PMAL(25)-PS (125) in Example 1, except that the polymerization degree of PS polymerization chains was 122.

Specific operation steps were as follows.

(1) 9 mL water was added into 1 g racemic asparagine monohydrate, followed by heating to 60° C. and dissolving under sufficient stirring. A clear and transparent supersaturated solution at a concentration of 111 mg/mL was obtained after hot filtering.

(2) 5 g solution obtained in step (1) was taken and added with 10.2 g of nano-inhibitor $Fe_3O_4$-(S)PMAL(12)-PS(122) (the content of the inhibitor segments was 0.25 wt % to the racemic substrate), followed by ultrasonic dispersion in 60° C. hot water for 15 min. After slowly cooling to room temperature, 0.5 mg seeds of R-asparagine monohydrate were added in.

(3) The solution obtained in step (2) was stood at 25° C. for 72 h.

(4) After crystallization, crystals precipitated at the bottom and an upper liquid was poured out. The remained crystals were dried under vacuum.

(5) The vessel containing the crystals was taken out, and a magnet (with a surface magnetic field strength >0.3 T) was used to approach the crystal mixture. The colored crystals were attracted by the magnet, while the colorless ones cannot be attracted by the magnet, i.e., resolution of the two enantiomers was effectuated. See FIGS. 6a and 6b.

The crystal yields and enantiomeric excess values (Table 1) were calculated in this example, and the enantiomeric excess values were characterized by chiral HPLC.

Example 8 Resolution of Racemic Asparagine Monohydrate

In this example, $Fe_3O_4$-(S)PMAL(40)-PS(122) was selected as a crystallization additive, and its preparation method was the same as that of $Fe_3O_4$—(S)PMAL(25)-PS (125) in Example 1, except that the polymerization degree of PMAL segments was 40.

Specific operation steps were as follows.

(1) 9 mL water was added into 1 g racemic asparagine monohydrate, followed by heating to 60° C. and dissolving under sufficient stirring. A clear and transparent supersaturated solution at a concentration of 111 mg/mL was obtained after hot filtering.

(2) 5 g solution obtained in step (1) was taken and added with 8.3 g of nano-inhibitor $Fe_3O_4$—(S)PMAL(40)-PS(122) (the content of the inhibitor segments was 0.25 wt % to the racemic substrate), followed by ultrasonic dispersion in 60° C. hot water for 15 min. After slowly cooling to room temperature, 0.5 mg seeds of R-asparagine monohydrate were added in.

(3) The solution obtained in step (2) was stood at 25° C. for 72 h.

(4) After crystallization, crystals precipitated at the bottom and an upper liquid was poured out. The remained crystals were dried under vacuum.

(5) The vessel containing the crystals was taken out, and a magnet (with a surface magnetic field strength >0.3 T) was used to approach the crystal mixture. The colored crystals were attracted by the magnet, while the colorless ones cannot be attracted by the magnet, i.e., resolution of the two enantiomers was effectuated. See FIGS. 6a and 6b.

The crystal yields and enantiomeric excess values (Table 1) were calculated in this example, and the enantiomeric excess values were characterized by chiral HPLC.

Example 9 Resolution of Racemic Asparagine Monohydrate

In this example, $Fe_3O_4$—(S)PMAL(59)-PS(129) was selected as a crystallization additive, and its preparation method was the same as that of $Fe_3O_4$—(S)PMAL(25)-PS (125) in Example 1, except that the polymerization degree of PMAL segments was 59.

Specific operation steps were as follows.

(1) 9 mL water was added into 1 g racemic asparagine monohydrate, followed by heating to 60° C. and dissolving under sufficient stirring. A clear and transparent supersaturated solution at a concentration of 111 mg/mL was obtained after hot filtering.

(2) 5 g solution obtained in step (1) was taken and added with 7.6 g of nano-inhibitor $Fe_3O_4$—(S)PMAL(59)-PS(129) (the content of the inhibitor segments was 0.25 wt % to the racemic substrate), followed by ultrasonic dispersion in 60° C. hot water for 15 min. After slowly cooling to room temperature, 0.5 mg seeds of R-asparagine monohydrate were added in.

(3) The solution obtained in step (2) was stood at 25° C. for 72 h.

(4) After crystallization, crystals precipitated at the bottom and an upper liquid was poured out. The remained crystals were dried under vacuum.

(5) The vessel containing the crystals was taken out, and a magnet (with a surface magnetic field strength >0.3 T) was used to approach the crystal mixture. The colored crystals were attracted by the magnet, while the colorless ones cannot be attracted by the magnet, i.e., resolution of the two enantiomers was effectuated. See FIGS. 6a and 6b.

The crystal yields and enantiomeric excess values (Table 1) were calculated in this example, and the enantiomeric excess values were characterized by chiral HPLC.

Example 10 Resolution of Racemic p-Hydroxyphenylglycine p-Toluenesulfonate

In this example, $Fe_3O_4$—(S)PMPA(45)-PS(115) prepared in Example 2 was selected as a crystallization additive.

Specific operation steps were as follows.

(1) 951 mg p-toluenesulfonic acid monohydrate was added into 10 mL deionized water. 500 mg racemic p-hydroxyphenylglycine p-toluenesulphonate was taken and dissolved in 2 mL of the above solution. The temperature was elevated to 60° C., and the racemic p-hydroxyphenylglycine p-toluenesulphonate was dissolved under sufficient stirring. A clear and transparent supersaturated solution was obtained after hot filtering.

(2) 7.3 g of nano-inhibitor $Fe_3O_4$—(S)PMPA(45)-PS (115) (the content of the inhibitor was 0.25 wt %) was added into the above solution, followed by ultrasonic dispersion in 60° C. hot water for 15 min. After slow cooling to room temperature, 0.5 mg seeds of R-p-hydroxyphenylglycine p-toluenesulphonate were added in.

(3) The solution obtained in step (2) was stood at 25° C. for 72 h.

(4) After crystallization, crystals precipitated at the bottom and an upper liquid was poured out. The remained crystals were dried under vacuum.

(5) The vessel containing the crystals was taken out, and a magnet (with a surface magnetic field strength >0.3 T) was used to approach the mixed crystals. The colored crystals were attracted by the magnet, while the colorless ones cannot be attracted by the magnet, i.e., resolution of the two enantiomers was effectuated.

TABLE 1

Resolution results with different additives

| Example | Standing time/D | Polymer content/% | Crystal | Yield/% | e.e value/% | Total yield/% |
|---|---|---|---|---|---|---|
| 3 | 3 | 0.25 | R (nonmagnetic) | 14.6 | 99.9 | 38.3 |
|   |   |   | S (magnetic) | 24.7 | 78.1 |   |
| 4 | 3 | 0.25 | R (nonmagnetic) | 17.0 | 98.3 | 39.8 |
|   |   |   | S (magnetic) | 23.8 | 91.5 |   |
| 5 | 3 | 0.25 | R (nonmagnetic) | 16.9 | 99.9 | 39.1 |
|   |   |   | S (magnetic) | 22.2 | 88.9 |   |
| 6 | 3 | 0.25 | R (nonmagnetic) | 16.9 | 99.7 | 40.7 |
|   |   |   | S (magnetic) | 23.8 | 89.5 |   |
| 7 | 3 | 0.25 | R (nonmagnetic) | 19.5 | 98.3 | 41.0 |
|   |   |   | S (magnetic) | 21.5 | 60.5 |   |
| 8 | 3 | 0.25 | R (nonmagnetic) | 20.4 | 88.1 | 42.2 |
|   |   |   | S (magnetic) | 21.8 | 88.1 |   |
| 9 | 3 | 0.25 | R (nonmagnetic) | 20.6 | 76.7 | 41.1 |
|   |   |   | S (magnetic) | 20.5 | 88.1 |   |

INDUSTRIAL APPLICATION

1. The present invention uses a kind of magnetic nano-inhibitors for the first time as an additive to introduce the microscopic properties of nanoparticles into the enantiomeric crystals, such that a macroscopic magnetic difference is generated between two enantiomeric crystals. A new chiral separation method mimicking magnetic beneficiation has been effectuated.

2. The magnetic nano-inhibitor is obtained by co-assembly, the synthesis being simple. The polymer portion can be readily replaced to achieve the resolution of different conglomerates.

3. Shell crosslinking can provide a stable assembly structure, which is suitable for use in different crystallization systems and concentrations, and can be recycled efficiently.

4. The present invention requires simple operations. Only magnetic field is necessary in the resolution process. Simple devices are used, and automatic resolution can be achieved. This is beneficial for industrial, large-scale production.

The invention claimed is:

1. A core-shell nanocomposite, which is formed by co-assembly of an amphiphilic polymer and hydrophobically modified magnetic nanoparticles, with a hydrophobically modified magnetic nanomaterial as its core and the amphiphilic polymer as its shell,
    wherein hydrophilic segments in the amphiphilic polymer are located at an outermost layer of the shell;
    wherein a crosslinking reaction is carried out between the hydrophilic segments to form a cross-linked shell;
    wherein the hydrophilic segments in the amphiphilic polymer are at least one selected from the group consisting of the following structural formulas:

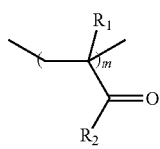

formula a

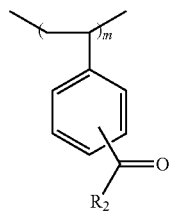

formula b

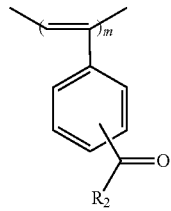

formula c wherein $R_2$ in formulas a-c is a functional group capable of being adsorbed on a crystal surface of a crystal to be resolved through non-covalent bond interaction, thus inhibiting crystallization and the following enrichment to promote nucleation;
wherein $R_1$ in formula a is at least one selected from the group consisting of methyl and hydrogen atoms;
wherein the hydrophobic segments in the amphiphilic polymer comprise at least one polymer selected from the group consisting of hydrophobic polymers, block copolymers comprising repeating units of the hydrophobic polymers, random comprising repeating units of the hydrophobic polymers, graft copolymers comprising repeating units of the hydrophobic polymers, and hyperbranched polymers comprising repeating units of the hydrophobic polymers;
further wherein the hydrophobic polymers comprise least one polymer selected from the group consisting of polystyrene, polyethylene, polypropylene, polybutadiene, polyisoprene, polydimethylsiloxane, polymethylhydrosiloxane, polymethacrylate, polymethacrylamide, polyamide, polyimide, polyformaldehyde, polycarbonate, cellulose, and derivatives thereof; and
wherein in formulas a-c, m represents the polymerization degree of the hydrophilic segments and ranges from 10 to 60.

2. The core-shell nanocomposite according to claim 1, wherein:
    $R_2$ in formulas a-c is at least one selected from the group consisting of the following groups:

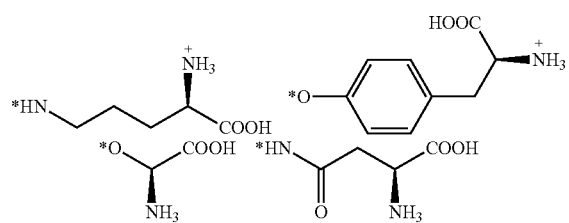

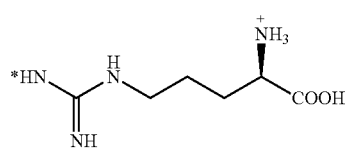

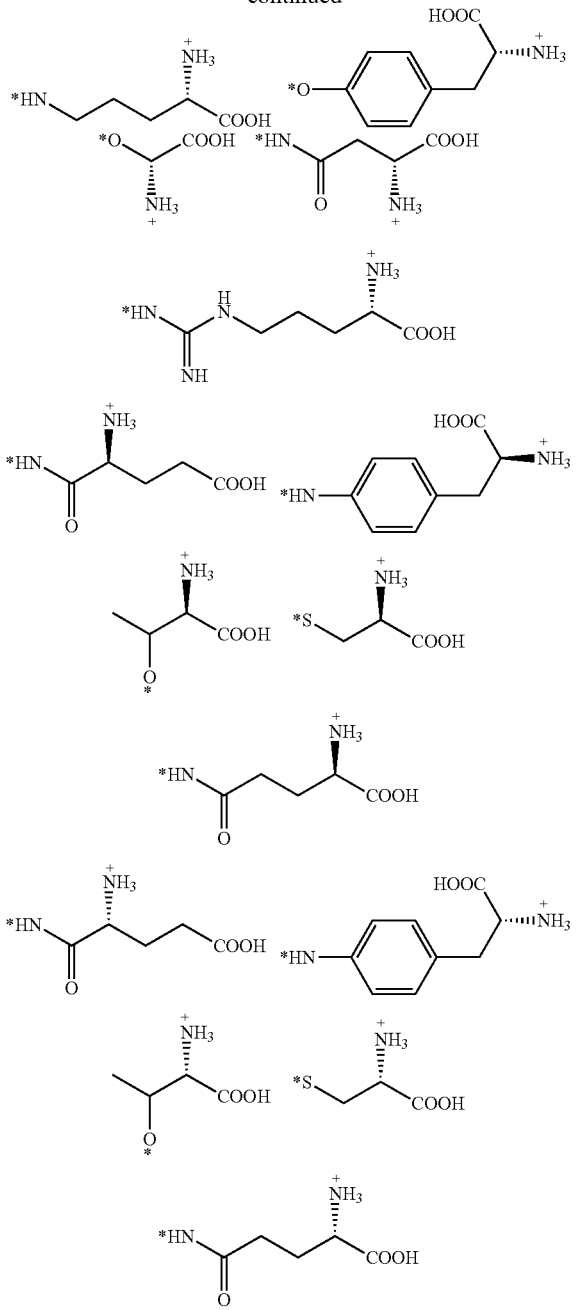

wherein in the above groups, * represents a bonding position.

3. The core-shell nanocomposite according to claim 1, wherein the magnetic nanomaterial is selected from magnetic nanoparticles formed by the following materials: Fe, Co, Ni, FePt, CoPt, FeAu, FePd, SmCo$_5$, Fe$_3$O$_4$, γ-Fe$_2$O$_3$, M$_1$Fe$_2$O$_4$, MO·6Fe$_2$O$_3$, and M$_2$Fe$_{12}$O$_{19}$, wherein M$_1$ in M$_1$Fe$_2$O$_4$ represents Zn, Mn, Ni, or Co, and M$_2$ in M$_2$Fe$_{12}$O$_{19}$ represents Ba or Sr;

wherein the magnetic nanoparticles have a diameter in the range from 3 nm to 500 nm; and wherein hydrophobic molecules used in the hydrophobically modified magnetic nanomaterial are at least one selected from the group consisting of oleic acid, oleamine, pyrrolidone, 11,11-dihydroxymethyl undecane, poly(tetravinylpyridine), and block copolymers of poly(tetravinylpyridine) and polyethylene.

4. A method for preparing the core-shell nanocomposite according to claim 1 comprising the steps of:
   1) dissolving the amphiphilic polymer in a cosolvent to obtain an amphiphilic polymer solution; dispersing the hydrophobically modified magnetic nanoparticles in a cosolvent to obtain a dispersion of the hydrophobically modified magnetic nanoparticles; and
   2) mixing the amphiphilic polymer solution with the dispersion of the hydrophobically modified magnetic nanoparticles in proportion to form a mixed solution, and then adding deionized water to the mixed solution until a stable assembly is formed;

wherein in step 1), the cosolvent is at least one selected from the group consisting of dimethyl sulfoxide (DMSO), N,N-dimethylformamide, tetrahydrofuran, dioxane, CH$_3$CN, acetone, methanol, ethanol, and isopropanol;

wherein in step 2), the mass ratio of the amphiphilic polymer to the hydrophobically modified magnetic nanoparticles in the mixed solution is in the range from 1:0.1 to 1; and further wherein in step 2), the deionized water is dropwise added into the mixed solution, and the volume ratio of the mixed solution to the deionized water is in the range from 1:2 to 8;

wherein the method further comprises the step of adding a crosslinking agent into a reaction system in which the stable assembly is formed to perform a shell crosslinking reaction, followed by dialysis in pure water to remove an organic solvent and unreacted small molecules, centrifugal separation, and freeze drying, and wherein the crosslinking agent is at least one selected from the group consisting of 1-(3-dimethylaminopropyl)-3-ethylcarbodiimide hydrochloride and glycol bis 2-aminoethyl ether.

5. A chiral resolution method mimicking magnetic beneficiation, comprising the steps of:
   (1) formulating a racemic substrate to be resolved into a supersaturated solution, followed by hot filtration;
   (2) adding the core-shell nanocomposite of claim 1 to the supersaturated solution, followed successively by ultrasonic dispersion, cooling to a crystallization temperature, addition of an optical pure seed of the racemic substrate to be resolved, and a standing is performed, wherein if the core-shell nanocomposite has S-hydrophilic segments, R-optically pure seeds are added, or otherwise, S-seeds are added;
   (3) obtaining mixed crystals of colored crystals and colorless crystals at the end of crystallization; and
   (4) approaching the mixed crystals with a magnet, wherein the colored crystals of one enantiomer is attracted by the magnet, while the colorless crystals of the other enantiomer is not attracted by the magnet to effectuate resolution of two enantiomers.

6. The method according to claim 5, wherein the method further comprising:
   dissolving the colored crystal in water; and
   recycling the core-shell nanocomposite by magnetic attraction, wherein the recycled core-shell nanocomposite is reused after being washed.

7. The method according to claim 5 wherein in step (1), the racemic substrate is asparagine monohydrate with a concentration in the range from 50 mg·mL$^{-1}$ to 150 mg·mL$^{-1}$.

8. The method according to claim 5, wherein the substrate to be resolved is asparagine monohydrate or threonine, and the hydrophilic segments of the amphiphilic polymer in the core-shell nanocomposite are poly($N^6$-methacryloyl-S-lysine hydrochloride); or the substrate to be resolved is p-hydroxyphenylglycine p-methylbenzene sulfonate, and the hydrophilic segments of the amphiphilic polymer in the core-shell nanocomposite are poly(p-methacryloyl-S-phenylalanine hydrochloride).

9. The method according to claim 5, wherein
in step (2), the core-shell nanocomposite accounts for 0.1-2.0 wt % of the racemic substrate to be resolved;
the amount of the optically pure seeds of the racemic substrate added accounts for 0.1-0.5 wt % of the racemic substrate to be resolved; and
the ultrasonic dispersion is performed in water at a temperature in the range from 40° C. to 60° C., at a power in the range from 40 KHz to 80 KHz, and for a period in the range from 15 min to 60 min; and
wherein the standing is performed at a temperature in the range from 0° C. to 40° C. for a period in the range from 6 h to 144 h.

\* \* \* \* \*